United States Patent [19]

Puderbaugh et al.

[11] 4,037,836
[45] July 26, 1977

[54] RESPIRATORY EXERCISER

[75] Inventors: George Puderbaugh, Manlius; Stanley Erman, East Syracuse, both of N.Y.

[73] Assignee: Diemolding Corporation, Canastota, N.Y.

[21] Appl. No.: 666,221

[22] Filed: Mar. 12, 1976

[51] Int. Cl.$^2$ ............................................. A63B 23/00
[52] U.S. Cl. .................................................... 272/99
[58] Field of Search .......................... 272/99; 128/2.08

[56] References Cited

U.S. PATENT DOCUMENTS

| 393,869 | 12/1888 | Warren | 272/99 X |
|---|---|---|---|
| 894,337 | 7/1908 | Morris | 128/2.08 |
| 2,100,898 | 11/1937 | Brenett | 128/2.08 X |
| 3,695,608 | 10/1972 | Hanson | 272/99 |
| 3,720,202 | 3/1973 | Cleary | 128/2.08 |

FOREIGN PATENT DOCUMENTS

| 8,662AD | 4/1903 | United Kingdom | 272/99 |

*Primary Examiner*—Jerome Schnall

*Attorney, Agent, or Firm*—Bruns & Jenney

[57] ABSTRACT

A respiratory exerciser particularly for encouraging deeper inhalation by post-surgical patients. The exerciser includes a transparent cylinder that is adapted to be supported in a vertical position. A lightweight ball is positioned in the cylinder which is provided with closure members at its upper and lower ends. The closure member for the upper end of the cylinder has a pair of apertures therethrough, and an open-ended tube is slidably mounted in one of the apertures so that it projects down into the cylinder. A flexible inhalation tube is connected to the other closure member aperture and by inhaling air through this tube the patient can cause the ball to rise in the vertical cylinder. Moving the open-ended tube up or down in its aperture varies the distance that it projects into the cylinder, and this in turn varies the degree of difficulty in raising the ball. Easily visible graduations on the cylinder enable the patient to see how high he is raising the ball and thus give a measurement of his progress.

4 Claims, 1 Drawing Figure

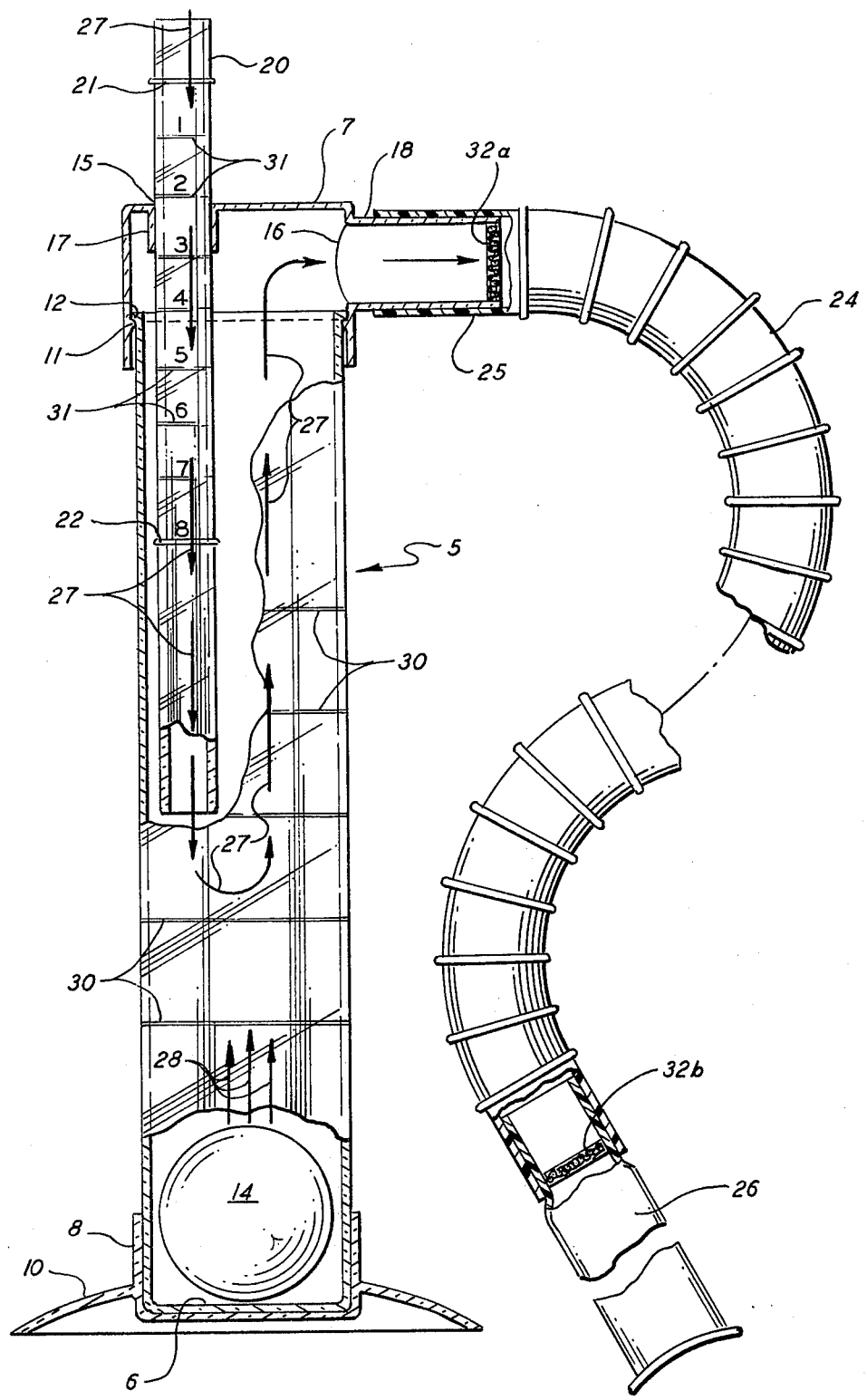

RESPIRATORY EXERCISER

BACKGROUND OF THE INVENTION

This invention relates generally to exercising devices, and has particular reference to a novel device for exercising the lungs.

After chest surgery, it is frequently very painful for the patient to breathe and, in addition, the patient may be so weakened that breathing is difficult. In such cases, the patient tends to breathe shallowly and deeper inhalation must be encouraged to help prevent lung congestion which can lead to pneumonia. Deeper breathing also helps to recondition muscles and aids in the healing process.

Lung exercising devices, or respiratory exercisers, have been developed heretofore both for medical use as noted above and non-medical use such as improving breath control for singing or playing a musical instrument. Devices of this type have also been devised purely for amusement. In the great majority of the respiratory exercisers of the prior art, the user exhales or blows into the device rather than inhaling through it as in the present invention. In fact the only prior inhalation device known to the applicant is disclosed in U.S. Pat. No. 393,869, issued Dec. 4, 1888 to C. E. Warren.

Like the present invention, several of the prior art respiratory exercisers employ a lightweight ball, such as a ping pong ball, as a visual indicator. These are U.S. Pat. Nos. 2,100,898; 3,695,608 and 3,720,202. However, each of these is an exhalation device and none operate in the manner of the device disclosed herein.

SUMMARY OF THE INVENTION

The inhalation respiratory exerciser of the instant invention comprises a rigid transparent cylinder that is adapted to be supported in a vertical position. A lightweight ball is positioned in the cylinder which is provided with closure members at its upper and lower ends. The upper end closure member has a pair of apertures therethrough, each of which is encircled by a projecting integral sleeve or nipple. The axis of one of these sleeves is offset from but substantially parallel to the axis of the cylinder and an elongated open-ended tube is slidably mounted in this sleeve.

A flexible inhalation tube is connected to the other aperture sleeve and by inhaling air through this tube the patient can cause the ball to rise in the cylinder. The slidably mounted open-ended tube projects down into the cylinder and the distance that it projects can be varied to vary the degree of difficulty in raising the ball. The cylinder is provided with graduation marks that enable the patient to see how high he is raising the ball and thus to measure his progress.

BRIEF DESCRIPTION OF THE DRAWINGS

The single FIGURE of the drawing is a side elevation, with portions in section, of a respiratory exerciser embodying the invention.

DESCRIPTION OF THE PREFERRED EMBODIMENTS

Having reference now to the drawing, the respiratory exerciser comprises a rigid, transparent cylinder 5 having an integral bottom 6 that forms a closure member for its lower end and a removable cap 7 that normally serves as a closure member for its upper end. The lower end of the cylinder fits into a cup-shaped member 8 that is formed with an outwardly projecting annular flange 10 for supporting the cylinder 5 in an upright position. The removable cap 7 has an internal bead 11 that snaps over an external bead 12 at the upper end of the cylinder to releasably secure the cap in position on the cylinder.

Positioned in the cylinder 5 is a lightweigt ball 14, such as a ping pong ball, there being clearance space between the ball and the inside of the cylinder wall as shown. The top cap 7 has apertures 15,16 in its top and side walls, respectively, and these are encircled by integral sleeves or nipples 17,18. Sleeve 18 projects outwardly while sleeve 17 projects inwardly, the axis of the latter sleeve being offset from but substantially parallel to the axis of cylinder 5.

An open-ended tube 20 is slidably mounted in the sleeve 17 and projects down into the cylinder 5 as indicated. This tube may be provided with upper and lower circumferential beads 21,22 to prevent the tube from being pushed all the way into or completely withdrawn from the cylinder. A flexible inhalation tube 24 is releasably connected to the cap 7 by a sleeve fitting 25 that telescopically engages the sleeve 18. At its other end, the tube 24 is provided with a mouthpiece 26 which can if desired be disposable.

In use, the cylinder 5 is placed on a table or other support close to the patient. When the patient inhales through the flexible tube 24, air is drawn into the cylinder 5 through the tube 20 as indicated by the arrows 27. The aerodynamic flow thus created in the cylinder causes the ball 14 to rise as indicated by arrows 28. The harder or more deeply the patient inhales, the higher the ball will rise, and the cylinder is provided with easily visible graduation lines 30 so that the patient can have a measurement of the height to which he is able to raise the ball.

When the slidably mounted tube 20 is pushed down into the cylinder as far as it will go, i.e. when its upper bead 21 engages the top of the cap 7, it is easier for the patient to raise that ball than when the tube is pulled out of the cylinder as far as it will go, i.e. when its lower bead 22 engages the lower edge of sleeve 17. Tube 20 is therefore also provided with a series of graduation lines 31 for moving the tube in measured steps from the easiest to the most difficult position for raising the ball. If desired, the cylinder graduation lines 30 and tube graduation lines 31 can be calibrated and coordinated so that for any given setting they will indicate the actual air volume inhaled into the lungs when the ball 14 is held at a graduation line 30 for a definite period of time as, for example, three or four seconds. It may be clinically advantageous to be able to make this information available to the inhalation therapist and attending physician.

In its preferred form the inhalation tube 24 includes a pair of relatively coarse filters 32a and 32b respectively located in the fitting 25 and in the mouthpiece 26, the filters being provided to prevent any foreign matter from entering the lungs of the patient.

From the foregoing description, it will be apparent that the invention provides a simple yet very effective respiratory exerciser of novel construction. As will be apparent to those familiar with the art, the invention may be embodied in other specific forms without departing from the spirit or essential characteristics thereof.

We claim:

1. A respiratory exerciser comprising an upright tube closed at its lower end, a closure member for the upper end of the tube, a lightweight ball positioned in the tube, the closure member having a pair of apertures therethrough, an elongated open-ended tube slidably mounted in one of the apertures and projecting down into the upright tube, the axis of said open-ended tube being parallel to but offset from the vertical axis of said upright tube, and an inhalation tube one end of which is in communication with the other aperture whereby a user of the exerciser by inhaling air through the inhalation tube can cause the ball to rise in the upright tube, the degree of difficulty in raising the ball being controlled by moving the open-ended tube up or down in its aperture.

2. A respiratory exerciser comprising a normally upright, rigid transparent cylinder having a base at its lower end to aid in supporting the cylinder in an upright position, a closure member for each of the upper and lower ends of the cylinder, the lower end of the cylinder being closed by the lower end closure member, a lightweight ball positioned in the cylinder, the upper end closure member having a pair of apertures therethrough, each aperture being encircled by a projecting integral sleeve, the axis of at least one sleeve being offset from but substantially parallel to the axis of the cylinder, an elongated open-ended tube slidably mounted in said one sleeve and projecting downwardly into the cylinder, and a flexible inhalation tube releasably connected to the other aperture sleeve whereby a user of the exerciser by inhaling air thorugh the inhalation tube can cause the ball to rise in the cylinder the distance that the open-ended tube projects into the cylinder can be varied by moving the tube up or down in its aperture sleeve to vary the degree of difficulty in raising the ball.

3. An exerciser as defined in claim 2 wherein the cylinder has graduation marks so that the height to which the ball rises can be measured.

4. An exerciser as defined in claim 2 wherein the flexible inhalation tube includes a disposable mouthpiece.

* * * * *